United States Patent
Nakaie et al.

(10) Patent No.: US 7,193,039 B2
(45) Date of Patent: Mar. 20, 2007

(54) SYNTHESIS OF A POTENT PARMAGNETIC AGONIST (EPM-3) OF THE MELANOCYTE STIMULATING HORMONE CONTAINING AMINO ACID-TYPE STABLE FREE RADICAL

(75) Inventors: Clovis Ryuichi Nakaie, Sao Paulo (BR); Simone Dos Reis Barbosa, Sao Paulo (BR); Eduardo Maffud Cilli, Sao Paulo (BR); Maria Tereza Lamy-Freund, Sao Paulo (BR); Armando Siuiti Ito, Sao Paulo (BR); Maria Aparecida Visconti, Sao Paulo (BR); Ana Maria De Lauro Castrucci, Sao Paulo (BR)

(73) Assignee: Conselho Nacional de Desenvolvimento Cientifico E Technologico-CNPQ, Distrito Federal (BR)

(*) Notice: Subject to any disclaimer, the term of this patent is extended or adjusted under 35 U.S.C. 154(b) by 475 days.

(21) Appl. No.: 10/168,391

(22) PCT Filed: Dec. 22, 2000

(86) PCT No.: PCT/BR00/00161

§ 371 (c)(1),
(2), (4) Date: Oct. 28, 2002

(87) PCT Pub. No.: WO01/46217

PCT Pub. Date: Jun. 28, 2001

(65) Prior Publication Data

US 2003/0212251 A1    Nov. 13, 2003

(30) Foreign Application Priority Data

Dec. 22, 1999 (BR) .................................... 9906090

(51) Int. Cl.
A61K 38/04 (2006.01)
(52) U.S. Cl. ..................................................... 530/327
(58) Field of Classification Search .................. None
See application file for complete search history.

(56) References Cited

OTHER PUBLICATIONS

Barbosa et al "First synthesis of a fully active spin-labled peptide hormone" FEBS Letters, 1999, vol. 446, pp-45-48.*
K. Hofmann et al., (1961) "Studies on Polypeptides. XX. Synthesis and Corticotropic Activity of a Peptide Amide Corresponding to the N-Terminal Tridecapeptide Sequence of the Corticotropins," *Journal of the American Chemical Society* 83, pp. 2289-2291.
A. Rassat et al., (1967) "No. 145-Nitroxydes. XXIII-Préparation d'aminoacides radicalaires et de leurs sels complexes," *Bull. Soc. Chim. Fr.* 815, pp. 815-817.
E. Gross et al., (1980) "The Peptides: Analysis, Synthesis and Biology vol. 2 Special Methods in Peptide Synthesis, Part A," *Academic Press*.
C. R. Nakaie et al. (1981) "pH Dependence of EPR Spectra of Nitroxides Containig Ionizable Groups," *Brazilian J. Med. Biol. Res.* 14, pp. 173-180.
E. London et al. (1981) "Fluorescence Quenching in Model Membranes. 1. Characterization of Quenching Caused by Spin-Labeled Phospholipid." *Journal of the American Chemical Society* 26(7), pp. 1932-1938.
C. R. Nakaie et al. (1983) "Synthesis and Properties of Spin-Labeled Angiotensin Derivatives," *Biochimica et. Biophysica Acta* 742, pp. 63-71.
M. Castrucci et al. "Melanotropin Bioassays: In Vitro and In Vivo Comparisons," *General and Comparative Endocrinology* 55, pp. 104-111.
D. N. Chaturvedi et al. (1985) "Synthesis and Biological Evaluation of the Superagonist [N$^\alpha$-Chlorotriazinylaminofluorescein-Ser[1], Nle[4], D-Phe[7]]-α-MSH," *Journal of Pharmaceutical Sciences* 74(3), pp. 237-240.
L. J. Berliner et al. (1989) "Spin-Labeling-Theory and Applications," *Biological Magnetic Resonance* 8, Plenum Press.
M. Castrucci et al. (1990) "Melanotropic Peptide Antagonists: Recent Discoveries and Biomedical Implications," *Drugs of the future* 15, pp. 41-54.
K. G. Mountjoy et al. (1992) "The Cloning of a Family of Genes that Encode the Melanocortin Receptors," *Science* 257, pp. 1248-1251.
H. Vaudry et al. (1993) "The Melanotropic Peptides," *Annals of the New York Academy of Sciences* 680.
S. M. Miick et al. (1992) "Short Alanine-based Peptides May Form $3_{10}$-helices in Aqueous Solution," *Letters to Nature* 350, pp. 653-655.

(Continued)

*Primary Examiner*—Bruce R. Campell
*Assistant Examiner*—Roy Teller
(74) *Attorney, Agent, or Firm*—Morrison & Foerster LLP

(57) ABSTRACT

The present invention refers to the chemical synthesis and potentiality for application in several biochemical assays, of a potent agonist of the α-melanocyte stimulating hormone (α-MSH), labeled with an amino acid-type paramagnetic spin probe (Toac, or 2,2,6,6-tetramethylpiperidine-1-oxyl-amino-4-carboxylic acid), valuable for use in electron spin resonance and fluorescence allowing biochemical-clinical investigation of relevant physiological roles of α-MSH in animal organism. The referred analogue of the present invention, acetil-Toac$^0$-(Nle[4], DPhe[7])-α-MSH, where (Nle[4], DPhe[7])-α-MSH is nominated commercially as Melanotan™ and although containing a non-natural compound in its structure such as Toac, maintained entirely its potent agonist potency. Its integral activity associated with the fact that it is naturally fluorescent (due to the Trp residue of its sequence) give to this labeled analogue a unique potential for a great variety of investigations regarding relevant physiological roles already known of this neuroimmunomodulator.

11 Claims, 5 Drawing Sheets

OTHER PUBLICATIONS

S. D. Sharma et al. (1996) "Melanotropic Peptide-Conjugated Beads for Microscopic Visualization and Characterization of Melanoma Melanotropin Receptors," *Proc. Natl. Acad. Sci.* 93, pp. 13715-13720.

E. M. Cilli et al. (1996) "Correlation Between Solvation of Peptide-Resins and Solvent Properties," *J. Org. Chem.*, 61(25), pp. 8992-9000.

W. Fan et al. (1997) "Role of Melanocortinergic Neurons in Feeding and the Agouti Obesity syndrome," *Nature* 385(9), pp. 165-168.

R. Marchetto et al. (1993) "A Novel Spin-Labeled Amino Acid Derivative for Use in peptide Synthesis: (9-Fluroenylmethyloxycarbonyl)-2,2,6,6-tetramethylpiperidine-N-oxyl-4-amino-4carboxylic Acid," *Journal of the American Chemical Society* 115(23), pp. 11042-11043.

H. Wessels et al. (1998) "Synthetic Melanotropic Peptide Initiates Erections in Men with Psychogenic Erectile Dysfunction: Double-Blind, Placebo Controlled Crossover Study," *The Journal of Urology* 160, pp. 389-393.

\* cited by examiner

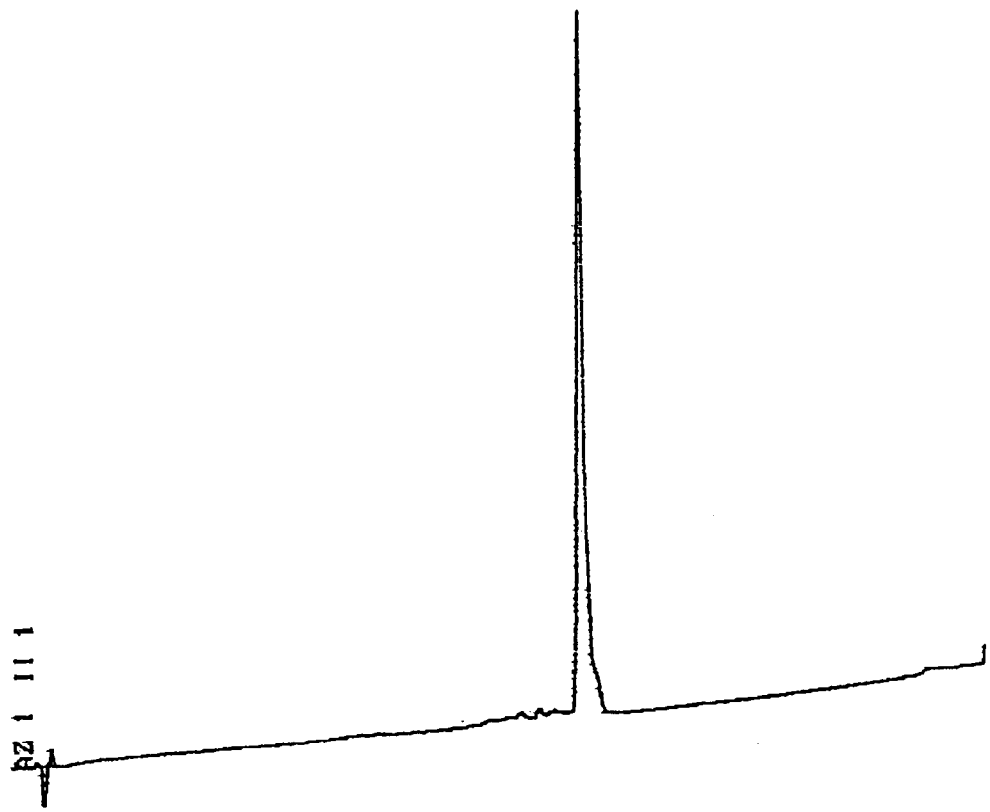
Figure 1: HPLC profile of the purified Ac-Toac$^0$-[(Nle$^4$, D-Phe$^7$)-α-MSH]. Conditions: ODS (4,6 x 150 mm) column and elution with solvent A (0,1% TFA in H$_2$O) and B (0,1% TFA in 60% acetonitrile/H$_2$O). Linear gradient from 5% to 95% B in 30 min, flow rate of 1,5 mL/min and detection at 220 nm.

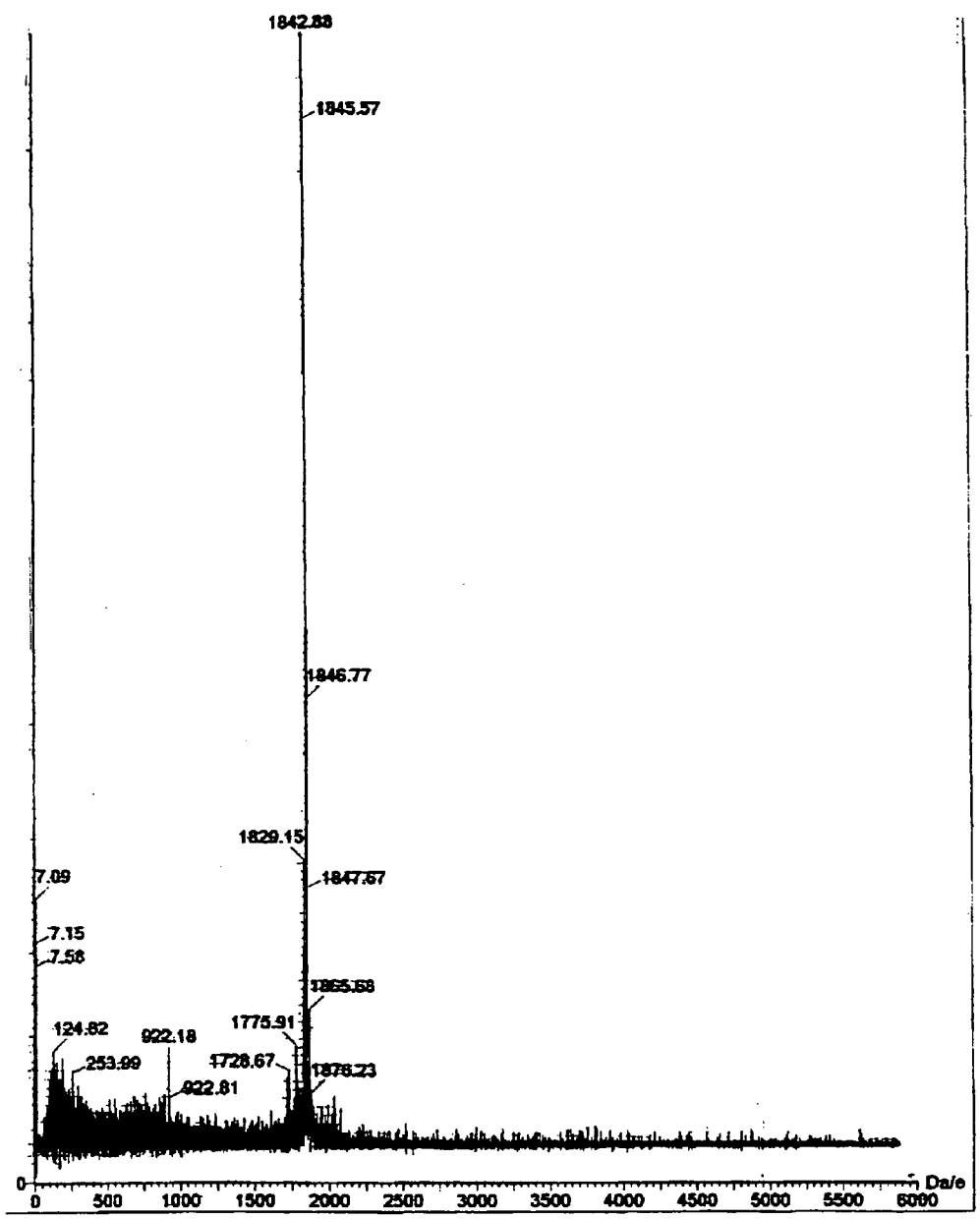
Figure 2 : Mass spectra of Ac-Toac⁰-[(Nle⁴, D-Phe⁷)-α-MSH].

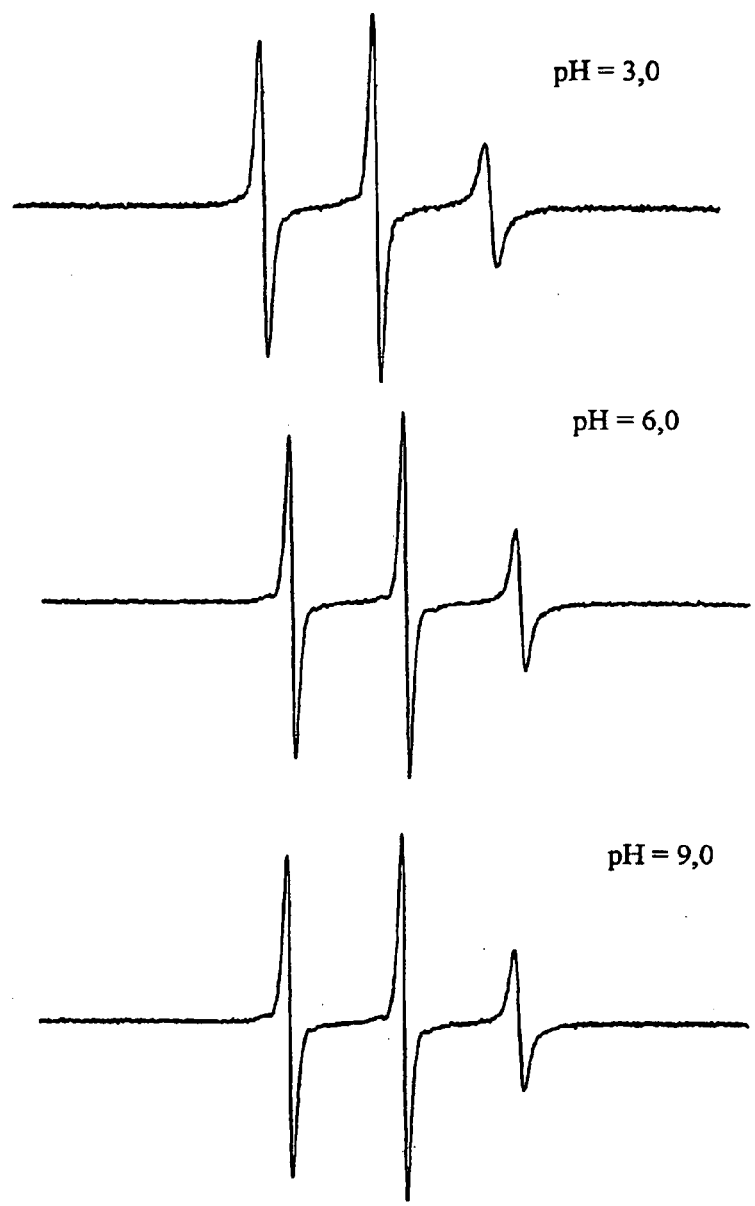
Figure 3: Electron spin resonance spectra of Ac-Toac⁰-[(Nle⁴, D-Phe⁷)-α-MSH] in aqueous solutions, pH=3,0; 6,0 and 9,0.

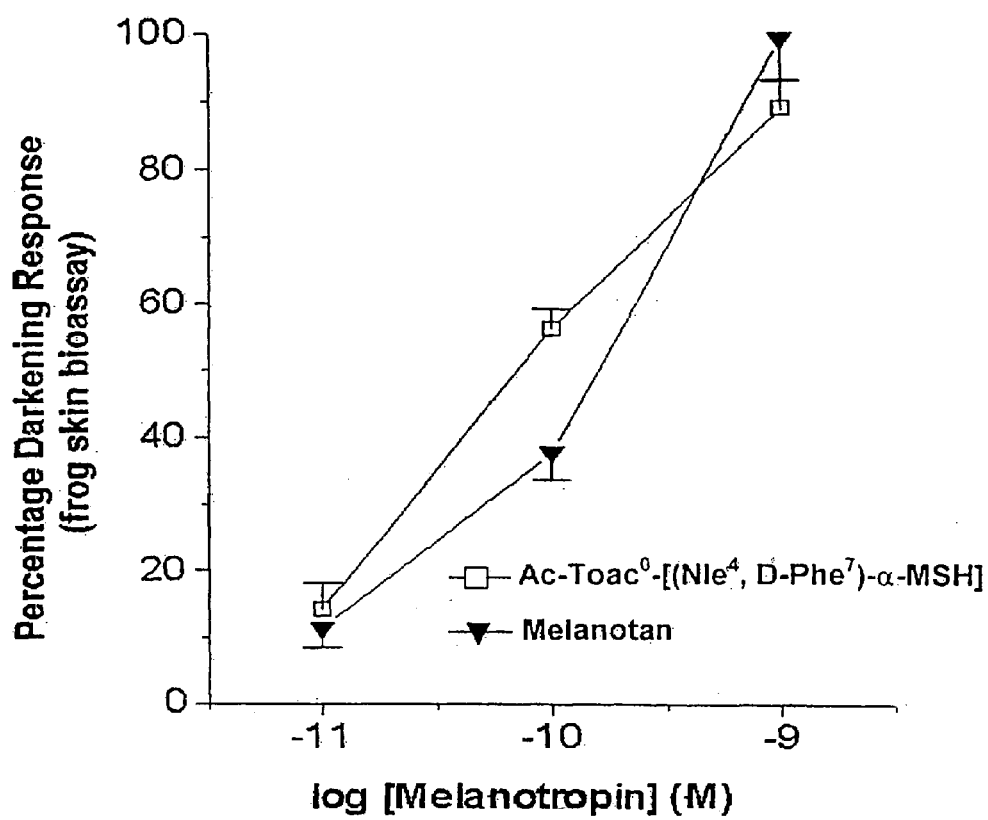
Figure 4: Dose-response curves for Ac-Toac$^0$-[(Nle$^4$, D-Phe$^7$)-α-MSH] as compared to the Melanotan, in frog Rana catesbeiana skin bioassay. Each point represents the mean (n = 8) ± S.E.M.(standard error of mean) darkening response at the concentration noted.

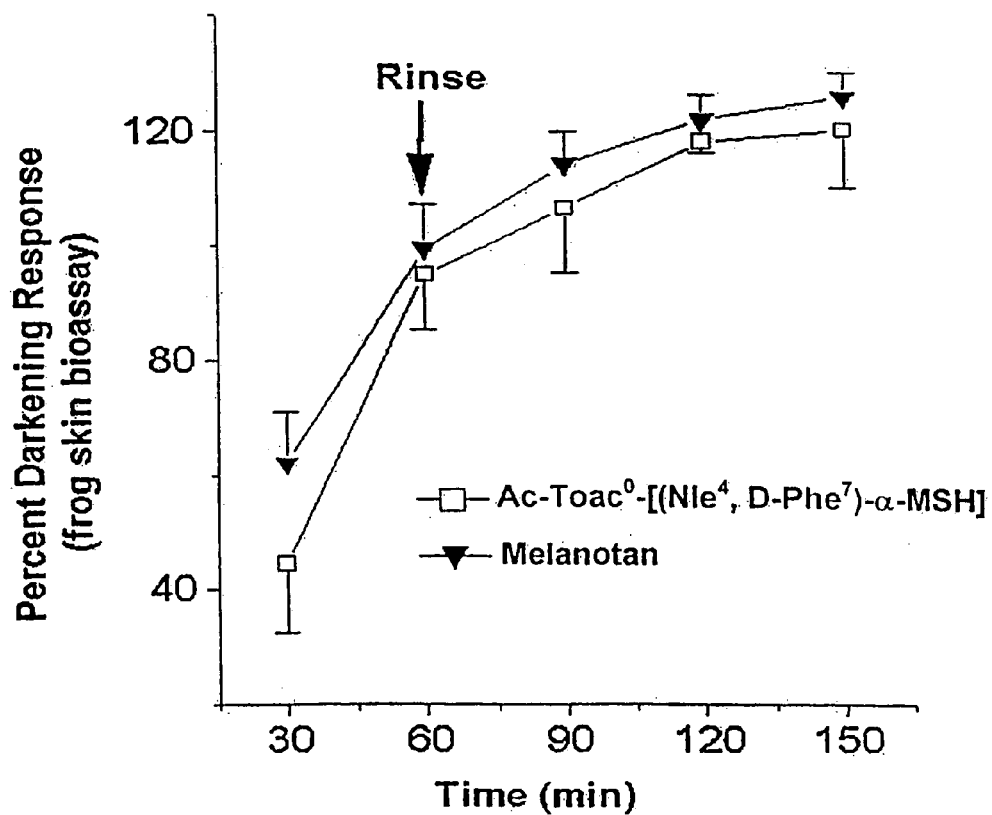
Figure 5: Reversal of the maximum response to Ac-Toac$^0$-[(Nle$^4$, D-Phe$^7$)-α-MSH] and Melanotan after removal of peptides and rinsing of the preparation (arrow). Each point is the mean (n=10) ± S.E.M., in *Rana catesbeiana* skin darkening bio assay at the times noted.

SYNTHESIS OF A POTENT PARMAGNETIC AGONIST (EPM-3) OF THE MELANOCYTE STIMULATING HORMONE CONTAINING AMINO ACID-TYPE STABLE FREE RADICAL

The present invention refers to the synthesis of a potent agonist of the melanocyte stimulating hormone (α-MSH) but containing a stable amino acid-type free radical (spin probe or spin label) that maintained entirely the original biological activity of the agonist.

The referred α-MSH agonist that was labeled with a paramagnetic marker is denominated Melanotan and contains the sequence [(Nle$^4$, D-Phe$^7$)-α-MSH]. This agonist presents 26 times higher potency than the original α-MSH hormone in some animals being also more resistant to proteases and presenting a more long-lasting activity. Due to the equipotency between Melanotan and its labeled analogue [acetyl-Toac$^0$-[Nle$^4$, D-Phe$^7$)-α-MSH] containing the spin probe amino acid Toac (see structural details later), make the latter peptide potentially useful for further studies in the biochemical-medical area and for better understanding of relevant α-MSH physiological functions. This is due to the fact that besides being paramagnetic, this Toac-containing Melanotan analogue is also fluorescent (it contains tryptophan in its structure) and as emphasized, presents the same potency of the Melanotan.

The melanocyte stimulating hormone (α-MSH) seems to be involved in several physiologic processes in the superior organism (vide gratia The Melanotropic Peptides, Vaudry, H & Eberle, N, eds., New York, 1993). Among these processes one may mention the effect upon the fetal growth, behavior, inflammation (v. g. Drugs of the Future, 15, 41[1990]), obesity [Nature 385, 165 (1997)], erectile function, [J. Urol. 160, 389 (1998)], etc. By any means, the more relevant effect of this hormone considered as a neuroimunemodulator, is related with the skin darkening effect (The Melanotropic Peptides, New York, [1993]).

The skin darkening of mammals and of other animals is basically controlled by the amount of melanine, a biological compound synthesized from the amino acid tyrosine and mediated by the enzyme tyrosinase. The melanine molecules are stored inside granules of cellular structures denominated melanocyte and it was observed that, the more aggregated these granules in the cells, the clearer the individual's skin will become. The control of this granular aggregation in the organism is made by a compound known as melatonine (N-acetyl-5-methoxy-triptamine). Contrariwise, darker skin is due to more dispersed melanine-containing granules in the cell and this dispersion control in the organism is made by the mentioned α-MSH.

This hormone is a peptide found in the pituitary gland of several animal species, including the human and its amino acid sequence already known, is represented below:

(Acetil-Ser-Tyr-Ser-Met-Glu-His-Phe-Arg-Trp-Gly-Lys-Pro-Val-CONH2)

Therefore, besides the importance of this hormone in the physiologic effects already mentioned, a better understanding of the α-MSH effect can be useful, for example, for possible elucidation of several diseases regarding irregular pigmentation of the skin. And in some of inferior beings, this peptide hormone is also very important because it allows alterations of the color of the skin in function of the ambient luminosity, thus facilitating the survival of some species.

The first chemical synthesis of this peptide was made some decades ago (v.g. J. Am. Chem. Soc. 83, 2289 [1961]) and recent researches on this important hormone aimed to clarify its action mechanism at the cellular membrane level, because its specific receptor was already characterized and found in different tissues and organs (Science 257, 1248 [1992]), including tumor cells (Proc. Natl. Acad. Scl. USA 93, 13715 [1996]). For this, several approaches are applied among which, many are spectroscopics that, besides furnishing conformational information of the hormone in solution, they can also supply details on interaction and positioning in synthetic or natural membranes.

In this context, a more potent α-MSH analogue was already developed (Melanotan, above mentioned) with the sequence [(Nle$^4$,D-Phe$^7$)-α-MSH] (v.g. Proc. Natl. Acad. Sci. USA 77/10, 5754 [1980]). This agonist has been for instance already labeled with fluorescent probes in specific positions of its sequence for further conformational and structural studies and its cellular receptor detection. (J. Pharm. Sci. 74, 237 [1985]).

However, there is not published yet a Melanotan analogue containing a paramagnetic compound (spin probe or spin label) and that has maintained entirely its original biological activity. The usefulness of the hormone labeling with this special type of marker molecule has the advantage of, for the first time, facilitates the application of the RPE method already mentioned [Spin Labeling—Theory and Applications, Berliner, L. J., New York, 1989] for the investigation of this important tridecapeptide hormone.

In contrast with other spectroscopic methods, the RPE permits the detection of conformational alterations of the hormone either in solution or associated with macrostructures such as membranes, based on spectral data that monitor the degree of motion of the molecule or of the system where the spin probe is bound. In addition, owing to the fluorescent quenching property of nitroxide function of the spin label [Biochemistry, 20, 1932 [1985]) allows to the RPE method a unique alternative approach for conjugation with the conventional fluorescence method. However, the most important pre-requisite in the strategy of introducing a spin marker in the α-MSH molecule or in any other biological molecule of interest is the need for maintenance of the original biological potency. It is not so probable as differently from the radioactive labeling of hormone which does not modify its chemical structure, a non-natural compound and with significant size is being inserted in the structure of the native hormone under study. Besides this pre-requisite it is also needed that the introduction of the spin probe in the hormone structure should be of such way that can closely reflect the peptide conformational features. For this reason, spin labels that bind to the hormone through a great amount of chemical bonds (long spin probes) and therefore, with high rotation freedom are not very appropriate. It is the case of some examples referred in the literature where long and flexible marker was used for RPE study of peptides, v.g Nature 359, 653 (1992). The ideal in the case would be, therefore, a paramagnetic probe that binds as much rigidly as possible to the peptide structure and directly in its skeleton through a peptide bond as it usually happens with amino acid residues.

By considering all these aspects, the inventors initiated the use, some decades ago, of an amino acid-type spin probe abbreviated as Toac (2,2,6,6-tetramethylpiperidine-1-oxyl-4-amino-4-carboxilic acid)—v.g. Bull. Soc. Chim. Fr. 815 (1967) in the peptide chemistry field and that it seems to attend partly, these requirements for binding more rigidly to the structure of the hormone. For containing the amine and carboxylic groups in a same carbon of the heterocyclic Toac structure (see the illustration below), this spin label can be introduced as an amino acid directly to the peptide backbone.

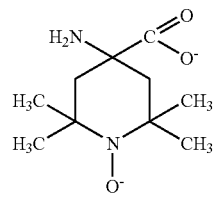

To make it possible to couple in a peptide sequence through the classic solid phase peptide synthesis methodology, (v.g Peptides: Analysis, Synthesis and Biology; Barany, G. and Merrifield, R. B. [1980]), the tert-butyloxycarbonil group was introduced (Boc) in the Toac amino group function, according to Braz. J. Med. Biol. Res 14, 173 (1981). Due to the lability of the free radical nitroxide group in strong acid medium present during the peptide synthesis method (trifluoroacetic acid), its introduction was only possible in the N-terminal, position of the peptide structure, v.g Biochim. Biophys. Acta, 742, 63 (1983). Later on, this limitation of the use of RPE in peptides was also overcome by the inventors, when using another Toac-amino group protection, the base labile 9-fluorenylmethyloxycarbonyl (Fmoc), in J. Am. Chem. Soc. 115, 11042 (1993). With this protecting group we demonstrated for the first time in the literature, a way of introducing the spin probe Toac at any internal positions of the peptide hormone structure, making possible therefore the substitution of any residue of amino acid of its original sequence for this paramagnetic compound. A great variety of examples of application of this strategy were later published but none of them had reported the synthesis of a spin labeled biologically active peptide that maintained entirely its potency.

Only more recently we submitted as for patenting purposes (v.g. "Synthesis of the first paramagnetic an active analogue of the melanocyte stimulating hormone containing amino acid-type stable free radical", PI 9900595, Feb. 22, 1999), the first paramagnetic analogue of a physiologically relevant peptide (α-MSH) containing the Toac compound equipotent to the native hormone. This result was further published [v.g. FEBS Lett., 446, 45–48 (1999)]. In this context, this spin labeling approach was extended to Melanotan hoping to have the maintenance of its original potency.

The invention here described the synthesis by chemical methods, of a Melanotan analogue labeled with Toac but that maintained 100% of its biological activity. This characteristic turns this peptide analogue potentially valuable and unique regarding the study of the melanotropic peptide functions, responsible for several physiological relevant effects in the superior organism.

As already detailed the chemical structure of the synthesized Melanotan analogue is: (Acetil-Toac-Ser-Tyr-Ser-Nle-Glu-His-DPhe-Arg-Trp-Gly-Lys-Pro-Val-$CONH_2$) that will be referred as to [acetyl-$Toac^0$-$[Nle^4$, D-$Phe^7$)-α-MSH] or EPM-3.

a) Chemical Synthesis

The strategy of coupling the spin probe Toac in the N-terminal portion is due to the fact that previous studies have shown that this position is less essential for the maintenance of melanotropic peptides. As the presence of the acetyl group in the amino terminal group of the sequence is also necessary for its activity, we carried out this acetylation step after the Toac incorporation. The general solid phase chemical methodology for peptide synthesis was applied for this sequence where the temporary protecting group Boc is used for peptide chain elongation bound to the starting polymer. The resin used was the methylbenzidril-amino-resin, a toluoylmethylamine-containing copolymer of styrene and 1% divinilbenzene for linking of the C-terminal residue of the sequence, v.g. Peptides 2, 45 (1981). The reactive side chains were protected temporary with appropriate chemical groups. In each synthetic cycle, the Boc protecting group is removed with 30% TFA (v/v) in dichloromethane (DCM) treatment for 30 min and the following deprotonation of the amine group of the sequence for coupling step is carried out in diisopropylethylamine, 10% v/v, in DCM for 10 minutes.

The coupling reaction of amino acids is usually done with the acylating agent diisopropylcarbodiimide in DCM/DMF (1:1) for about 2 hours. The monitoring of this important synthesis reaction is carried out with the ninhydrin test and if recoupling is needed, the acylating agent is changed for tetrafluoroborate-2-(1H-benzotriazolyl-1,1,3,3-tetramethyluronium) or TBTU. The choice of the solvent system for each synthesis cycle followed the method introduced recently by the inventors, based on a new solvent polarity parameter that considers the sum of the acceptor (AN) and donor (DN) electron properties of the solvents, v.g. J. Org. Chem. 61, 8992 (1996). The selected solvent for the α-MSH synthesis based on this study was N-methylpirrolidinone (NMP).

The introduction of the Toac probe was performed with its Fmoc derivative and followed the already mentioned synthesis strategy which allows the introduction of this spin label internally to the peptide sequence. The acetylation step was done using a large excess of acetic anhydride in DMF for 1 h and in general, we did not observe relevant difficulties in the assembly of this acetylated tetradecapeptide. The cleavage of peptide from the resin was carrried out in anhydrous HF for 90 min at 0° C. In this reaction, ethanediol was added for the Trp formyl-group removal and cresol and dimethylsulfide to minimize side reactions during this acid treatment. The proportion of these components was: HF:o-cresol:dimethylsulfide:ethanoditiol (8.5:0.5:0.5:0.5). After the cleavage the resin is rinsed with ethyl acetate for removal of by-products and the desired peptide was extracted from the resin with 5% AcOH and liophilyzed. A white powder material was obtained with a final yield of 83%.

a.1). Comparative Alkaline Treatment for the Reversion of Nitroxide Protonation After HF Cleavage The insertion of the Toac molecule in a peptide sequence needs an additional alkaline treatment for reversion of nitroxide protonation that occurs during HF cleavage. As there is not until the moment, any systematic study showing the most effective and fast method of this reversion, we decided to test comparatively different basic conditions for this reversion. It was observed that the more efficient reversion protocol was: aqueous ammonium hydroxide solution, pH 10 for 2 h at 50° C. The monitoring of the reversion rate was based on the analytical high pressure liquid chromatography (HPLC) retention time of both Toac protonated and unprotonated forms. Due to its higher polarity the protonated form eluted faster than the parent component.

a.2) Purification of the Peptide

The crude peptide submitted to the alkaline reversion was purified in preparative HPLC with a C18 column (25 for 300 mm) in acetonitrile/water gradient containing 1% of TFA. The main fraction isolated in this chromatogram yielded after lyophilyzation, 37 mg of a white powder, whose purity is represented in the analytical HPLC shown in FIG. 1.

The homogeneity of this material was also confirmed by mass spectroscopy with a MALDI-type equipment (matrix assisted desorption ionization) from Micromass. The FIG. 2 exhibits the expected 1843 molecular weight peak of the EPM-3 against 1664 of the native α-MSH. The correct composition of this sample was also checked by amino acid analysis in an Beckman, model 6300 analyzer. The following relative proportion of amino acid was found: (the theoretical values are among parentheses): 1.95 Ser (2), 1.03 Nle (1), 1.01 Glu (1); 0.96 His (1); 0.98 Phe (1); 0.97 Arg (1); 1.04 Trp (1); 0.97 Gly (1); 1.05 Lys (0); 0.95 For (1) and 1,01 Val (1). The acid hydrolysis carried out includes dissolution of the peptide in HCl (6 N) degassed (with $N_2$) solution containing 0.5% phenol and left for 72 h at 110° C. in a Pyrex capped vial. As the Trp residue is decomposed by this acid treatment, the peptide was hydrolized with the p-toluenosulfonic acid method. The peptide was submitted to this treatment for 72 h and further diluted with a pH 2.2 buffer before injecting in the amino acid analyzer column.

Besides all these analytic characterizations applied for the spin labeled peptide, the RPE spectroscopy was also used to confirm the paramagnetic signal of the sample. The FIG. 3 displays the RPE spectrum of the labeled hormone after purification and diluted in ammonium acetate solution (0.05 M, pH 5.0), comparatively to the free Toac in the same conditions.

b. Biological Activity Assay.

The biological activity assay of [acetyl-Toac$^0$-[Nle$^4$, D-Phe$^7$)-α-MSH] or EPM-3 was always carried out comparatively to the Melanotan. The classical method of measuring by reflectance the alteration in the frog skin pigmentation was assayed, v.g. Gen. Comp. Endocrinol. 55, 104 (1984). The potency of the synthesized hormone was determined through a dose-effect curve and long lasting activities were measured until a maximum of 3 h, after the peptide removal from the incubation system carried out with successive washes.

Briefly, the thigh's skin and the dorsal portion of the frog were removed and cut in pieces of 2×2 cm which were placed among two rings of PVC and maintained by 1 h in Ringer solution. After this period, the melanine granules aggregate in the melanocites and the skin become clearer. When α-MSH or its spin labeled analogue are added to the medium, there is a dispersion of the pigments in the cell, resulting in skin darkening. The change in the coloration is therefore monitored (decrease in the skin reflectance) in a Photovolt reflectometer. The result is expressed as percentage in relation to the initial value.

The labeled analogue is clearly a full Melanotan agonist with equivalent potency as it can be seen in the FIG. 4. In, addition, after the removal of the agonist and followed by several Ringer washings, the reversal of the maximum response for the labeled analogue was identical to the determined for Melanotan, that is, even after 2 h, the biological activity was maintained for both peptides (FIG. 5).

By containing the spin probe Toac in its structure and for fully maintaining the biological potency of Melanotan, the novel chemical product herein described and denoted [acetyl-Toac$^0$-[Nle$^4$, D-Phe$^7$)-α-MSH] or EPM-3 may be of practical application in the following situations:

1. As comparative model-compound for investigation of the active Melanotan and α-MSH conformations.

1.a) In Solution

The knowledge of the correct α-MSH action mechanism in vertebrates can be better investigated by using the Melanotan analogue [acetyl-Toac$^0$-[Nle$^4$, D-Phe$^7$)-α-MSH] or EPM-3. This is due to the fact that by containing a paramagnetic group in its structure, its conformational features may be evaluated with the RPE spectroscopic method. Initially, variations on pH, temperature, ionic strength and the amount of organic solvents in the medium can be performed in solution and analyzed as to the RPE spectra of this paramagnetic peptide hormone.

The influence of organic solvents trifluoroetanol (TFE) and hexafluoroisopropanol (HFPI), known to induce secondary structures as the α-helix might be also investigated. Complementarily to the RPE method, this conformational approach can be also carried out with other spectroscopic methods such as the circular dicroism, nuclear magnetic resonance and fluorescence. In these last two methods, For possessing the property of suppressing resonance or absorption/emission effects respectively, the paramagnetic peptide of the present patent may be employed in a great variety of comparative spectroscopic studies.

1.b) In Macrostructures Such as Artificial Bilayers and Membranes.

The above detailed conformational studies can be extended to internal regions of macrostructures such as lipid bilayers and artificial membranes. This approach will mimic the native hormone conformation when inserted in a common biological membrane. By taking into account an other property of the RPE method, the molecular association of paramagnetic compounds can be studied based on the spin-spin interaction phenomenon that occurs between spin probes but strongly dependent on the average distance among these molecules, v.g. Spin Labeling—Theory and Applications, (Berliner, L. J., New York, 1989). Besides the sensitivity to detect the molecular interactions inside these macrostructures, it is also possible to further estimate intermolecular distances, regardless the system.

2. As Molecular Probe for Detection, Quantification and Characterization Studies of α-MSH Receptor.

The utility of [acetyl-Toac$^0$-[Nle$^4$, D-Phe$^7$)-α-MSH] or EPM-3 will be indirectly evaluated in this approach. The Toac usefulness will be dependent of the fluorescence quenching effect induced by the nitroxide function. The use of radioactive or fluorescent agonists have been the most common strategy to localize, quantify and characterize membrane receptors. One may therefore detect and quantify receptor-containing cells and how they are positioned throughout cell membranes. The more appropriate method so far used for localization, quantification and characterization of membrane receptors use fluorescent agonists as this strategy is less dangerous and the agonist which will bind to the receptor presents higher chemical stability than the parent radioactive analogue. Thus, by taking into account the fluorescence quenching property, the Toac-labeled Melanotan will be useful for:

2.a) α-MSH Receptor Visualization, Localization and Characterization.

As fluorescent α-MSH or Melanotan analogues has been already synthesized for receptor binding studies, the use of EPM-3 fluorescent quenching property may be of value, for instance for checking receptor localization and quantification. As there are modern methods to visualize receptors in cell cultures, frozen cell slices and cell fragments in vitro or in vivo, one may predict a relevant EPM-3 utility for help elucidate the action mechanism of α-MSH when bound to the receptor.

2.b) Quantification of Cell Lineage Containing α-MSH Receptors.

This important information at receptor levels may be obtained by modern biochemical methods such as the flow citometry and where one can identify and characterize common cells lineages containing or not the α-MSH receptor.

2.c) Investigation of Receptor-fluorescent Hormone Binding.

The mechanism and the kinetics of interaction investigation of fluorescent α-MSH or Melanotan derivatives with the former receptor can be improved with the use of [acetyl-Toac$^0$-[Nle$^4$, D-Phe$^7$)-α-MSH]. This peptide will be also valuable for monitoring bindings of other analogues Or chemical products that possess the common property in binding to α-MSH receptor.

3. As Proteolytic Enzyme Substrate or Inhibitor

In the case where an evaluation the peptide hormone towards enzyme degradation is desired, the presence of Toac radical will be of value as it will supply details of molecular mobility related to enzymatic peptide degradation, either in solution or internally to several types of macrostructures (natural membranes, lipid bilayers, polymer beads, cells, etc).

The invention claimed is:

1. Acetyl-(2,2,6,6-tetramethylpiperidine-1-oxyl-4-amino-4-carboxylic acid) -Ser-Tyr-Ser-Met-Nle-Glu-His-DPhe-Arg-Trp-Gly-Lys-Pro-Val-CONH$_2$ (SEQ ID NO:1).

2. A method of synthesizing a paramagnetic and fully biologically active agonist of α-melanocyte stimulating hormone, comprising:
   introducing a paramagnetic group internally into α-melanocyte stimulating hormone peptide sequence by means of an acylating agent,
   wherein the α-melanocyte stimulating hormone peptide sequence is Ser-Tyr-Ser-Met-Nle -Glu-His-DPhe-Arg-Trp-Gly-Lys-Pro-Val-CONH$_2$ (SEQ ID NO:1); and
   wherein the paramagnetic group is derived from 2,2,6,6-tetramethylpiperidine-1-oxyl-4-amino-4-carboxylic acid.

3. The method of claim 2, further comprising introducing by a solid phase method an amino-terminal acetyl-group into the sequence after the introducing of the paramagnetic group, wherein tert-butyloxycarbonyl (boc) is used as a temporary α-amine group protector for peptide chain elongation and methyl-benzhydrylamine-resin and a styrene-1 % divinylbenzene copolymer containing toluyl-methylamine groups are used for coupling of the c-terminal residue of the sequence.

4. The method of claim 3, comprising boc group cleavage carried out by treatment in trifluoroacetic acid 30% (v/v) in dichloromethane for 30 minutes followed by the deprotonation of the amine group, carried out in basic diisopropylethylamine, 10% v/v in dichloromethane solution for 10 min.

5. The method of claim 3, comprising using as an acylating agent diisopropylcarbodiimide in dichloromethane/dimethylformamide (1:1) for about 2 hours, and monitoring the acylation with a colorimetric ninhydrin test.

6. The method of claim 5, further comprising recoupling with 2-(1H-benzotriazolyl-1,1,3,3-tetramethyluronium) tetrafluoroborate.

7. The method of claim 3, comprising using 9-fluorenylmethyloxycarbonyl as a protection agent to allow introduction of the spin probe internally to the peptide sequences and

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<221> NAME/KEY:
<222> LOCATION:
<223> OTHER INFORMATION: Synthetic Peptide
<220> FEATURE:
<222> LOCATION: 5
<223> OTHER INFORMATION: Xaa represents Norleucine
<220> FEATURE:
<222> LOCATION: 8
<223> OTHER INFORMATION: This is a D form of Phenylalanine

<400> SEQUENCE: 1

Ser Tyr Ser Met Xaa Glu His Phe Arg Trp Gly Lys Pro Val
1               5                   10
``` carrying out a final acetylation step using acetic anhydride in dimethylformamide for about 1 hour.

8. The method of claim 3, further comprising cleaving the synthesized peptide from the resin with anhydrous HF for about 90 min at 0° C., extracting the peptide from the resin with 5% acetic acid in water and lyophilizing the extracted peptide.

9. The method of claim 3, further comprising an alkaline treatment of crude peptide for nitroxide deprotonation and purification with the use of an acetonitrile/water gradient.

10. A method for detecting, quantifying or characterizing an α-melanocyte stimulating hormone receptor level in a tissue sample, comprising:

applying a reagent comprising Acetyl-(2,2,6,6-tetramethylpiperidine-1-oxyl-4-amino-4-carboxylic acid)-Ser-Tyr-Ser-Met-Nle-Glu-His-DPhe-Arg-Trp-Gly-Lys-Pro-Val-CONH$_2$ (SEQ ID NO:1) to the tissue sample; and determining a change of coloration in the tissue sample indicative of a presence, amount or activity of α-melanocyte stimulating hormone in the tissue sample.

11. A method for detecting, quantifying or characterizing an α-melanocyte stimulating hormone receptor level in a tissue sample, comprising:

applying a reagent comprising Acetyl-(2,2,6,6-tetramethylpiperidine-1-oxyl-4-amino-4-carboxylic acid)-Ser-Tyr-Ser-Met-Nle-Glu-His-DPhe-Arg-Trp-Gly-Lys-Pro-Val-CONH$_2$ (SEQ ID NO:1) to the tissue sample; and determining an amount of fluorescence quenching in the tissue sample by the reagent indicative of a presence, amount or activity of α-melanocyte stimulating hormone in the tissue sample.

* * * * *